United States Patent [19]
Lupu et al.

[11] Patent Number: 5,874,528
[45] Date of Patent: Feb. 23, 1999

[54] BINDING PEPTIDES WHICH INTERACT WITH LIGAND GROWTH FACTORS OF THE EPIDERMAL GROWTH FACTOR RECEPTOR AND ERBB-2 RECEPTOR

[75] Inventors: Ruth Lupu, Gaithersburg; Marc E. Lippman, Bethesda, both of Md.

[73] Assignee: Georgetown University, Washington, D.C.

[21] Appl. No.: 117,187

[22] PCT Filed: Apr. 29, 1993

[86] PCT No.: PCT/US93/04055

§ 371 Date: Oct. 27, 1994

§ 102(e) Date: Oct. 27, 1994

Related U.S. Application Data

[63] Continuation-in-part of Ser. No. 875,788, Apr. 29, 1992, abandoned, which is a continuation-in-part of Ser. No. 640,497, Jan. 14, 1991, abandoned, which is a continuation-in-part of Ser. No. 917,988, Jul. 24, 1992, abandoned, which is a continuation-in-part of Ser. No. 872,114, Apr. 22, 1992, abandoned, which is a continuation of Ser. No. 528,438, May 25, 1990, abandoned.

[51] Int. Cl.$^6$ ............................... C07K 7/52; C07K 7/00
[52] U.S. Cl. ............................ 530/317; 530/328; 514/11; 514/9; 514/8
[58] Field of Search ...................... 530/397, 395, 530/399, 317, 328; 514/8, 11, 9; 424/573

[56] References Cited

U.S. PATENT DOCUMENTS

| | | | |
|---|---|---|---|
| 4,933,294 | 6/1990 | Waterfield et al. | 435/4 |
| 5,030,565 | 7/1991 | Niman et al. | 530/387.7 |
| 5,367,060 | 11/1994 | Vandlen et al. | 530/399 |

OTHER PUBLICATIONS

Yamamoto et al, Nature, vol. 319, pp. 230–234, (Jan. 16, 1986).

*Primary Examiner*—Ponnathapura Achutamurthy
*Assistant Examiner*—T. D. Wessendorf
*Attorney, Agent, or Firm*—Banner & Witcoff, Ltd.

[57] ABSTRACT

The present invention relates to blocking peptides which are capable of binding to ligands for the erbB-2 receptor or the epidermal growth factor receptor (EGFR). The blocking peptides of the invention are used to detect the presence of such ligand molecules. In addition, the blocking peptides are useful in inhibiting or preventing the growth of adenocarcinoma cells which express the erbB-2 receptor or the EGFR.

2 Claims, 8 Drawing Sheets

BINDING PEPTIDES WHICH INTERACT WITH LIGAND GROWTH FACTORS OF THE EPIDERMAL GROWTH FACTOR RECEPTOR AND ERBB-2 RECEPTOR

RELATED APPLICATIONS

The present application is a national stage of a PCT application PCT/US 93/04055 which was filed Apr. 29, 1993, and is a continuation-in-part of U.S. application Ser. No. 07/875,788, filed Apr. 29, 1992 abandoned, which is a continuation-in-part of U.S. application Ser. No. 07/640, 497, filed Jan. 14, 1991 abandoned and a continuation-in-part of U.S. application Ser. No. 07/917,988, filed Jul. 24, 1992 abandoned, which is a continuation-in-part U.S. application Ser. No. 07/872,114, filed Apr. 22, 1992 abandoned, which is a continuation of U.S. application Ser. No. 07/528, 438, filed May 25, 1990, now abandoned. All of these applications are incorporated by reference in entirety.

BACKGROUND OF THE INVENTION

1. Field of the Invention

The invention relates to the field of blocking peptides which interact with ligand growth factor receptors. Specifically, the blocking peptides of the invention are capable of binding to ligands to the epidermal growth factor receptor and the erbB-2 receptor. The present invention further relates to the use of such blocking peptides in assays to detect the presence of ligand growth factors. Methods of using the blocking peptides of the invention as a means of inhibiting the growth of adenocarcinoma cells and for diagnosing cancer are also disclosed.

2. Review of Related Art

Transforming growth factor ligands belong to a family of heat and acid-stable polypeptides which allow cells to assume a transformed morphology and form progressively growing colonies in anchorage-independent growth assays (DeLarco, et al., *Proc. Natl. Acad. Sci. USA*, 75:4001–4005 (1978); Moses, et al., *Cancer Res.*, 41:2842–2848 (1981); Ozanne, et al., *J. Cell. Physiol.*, 105:163–180 (1980); Roberts, et al., *Proc. Natl. Acad. Sci. USA*, 77:3494–3498 (1980)). The epidermal growth factor receptor (EGFR) and its physiologic ligands, epidermal growth factor (EGF) and transforming growth factor alpha (TGFα), play a prominent role in the growth regulation of many normal and malignant cell types (Carpenter, G., *Annu. Rev. Biochem.*, 5:881–914 (1987)).

One role the EGF receptor system may play in the oncogenic growth of cells is through autocrine-stimulated growth. If cells express the EGFR and secrete EGF and/or TGFα then such cells could stimulate their own growth. Since some human breast cancer cell lines and tumors express EGFR (Osborne, et al., *J. Clin. Endo. Metab.*, 55:86–93 (1982); Fitzpatrick, et al., *Cancer Res.*, 44:3442–3447 (1984); Filmus, et al., *Biochem. Biophys. Res. Commun.*, 128:898–905 (1985); Davidson, et al., *Mol. Endocrinol.*, 1:216–223 (1987); Sainsbury, et al., *Lancet*, i: 1398–1402 (1987); Perez, et al., *Cancer Res. Treat.*, 4:189–193 (1984)) and secrete TGFα A (Bates, et al., *Cancer Res.*, 46:1707–1713 (1986); Bates, et al., *Mol. Endocrinol.*, 2:543–555 (1988)), an autocrine growth stimulatory pathway has been proposed in breast cancer (Lippman, et al., *Breast Cancer Res. Treat.*, 7:59–70 (1986) ).

An autocrine growth stimulatory pathway analogous to that proposed for epidermal growth factor receptor and its ligands may also be employed by a growing list of oncogene encoded transmembrane proteins that have structure reminiscent of growth factor receptors. This list includes the protooncogenes neu and its human equivalent erbB-2 or HER2 (Bargmann, et al., *Nature*, 319:226–229 (1986); Coussens, et al., *Science*, 230:1131–1139 (1985); Yamamoto, et al., *Nature*, 319:230–234 (1986); c-kit (Yarden, et al., *EMBO J.*, 6:341–3351 (1987); ros (Neckameyer, et al., *Mol Cell. Biol.*, 6:1478–1486 (1986); met (Park, et al., *Proc. Natl. Acad. Sci. USA*, 84:6379–6383 (1987); trk (Martin-Zanca, et al., *Nature*, 319:743–748 (1986); and ret (Takahashi, et al., *Mol. Cell. Biol.*, 7:1378–1385 (1987)). The erbB-2 and c-kit protooncogenes encode factors that display structural homology with EGFR (Yarden, et al., *Annu. Rev. Biochem.*, 57:443–478 (1988). Although erbB-2 and its related oncogene neu are related to EGFR, these proteins are distinct. For example, known EGFR ligands such as EGF and TGFα do not bind to erbB-2 receptor. (King, et al., *EMBO J.*, 7:1647 (1988); and Stern, et al., *EMBO J.*, 7:995 (1988).

Amplification or overexpression or both have been described for the c-erbB-2 gene in a number of human adenomas (Semba, et al., *Proc. Natl. Acad. Sci. USA*, 82:6497 (1985); Van de Vijver, et al., *Mol. Cell. Biol.*, 7:2019 (1987); Yokota, et al., *Oncogene*, 2:283 (1988); Slamon,et al., *Science* 244:707 (1989); Aasland, et al., *Br. J. Cancer*, 57:358 (1991); Cline, et al., *Cancer*, 60:2669 (1991)). Overexpression statistically correlates with short term relapse in breast (Slamon, et al., *Science*, 235:177 (1987); Walker, et al., Br. *J. Cancer*, 60:426 (1991); Wright, et at., *Cancer Res.*, 49:2087 (1991)), ovarian (Berchuck, et al., *Cancer Res.* 50:4087 (1990)) and gastric cancers (Yonomura, et al., ibid., 51:1034 (1991)). Moreover, overexpression of $p185^{erbB-2}$, the product of the erbB-2 oncogene, has been associated with tumor cell resistance to several cytotoxic mechanisms including actions of tumor necrosis factor on NIH 3T3, breast or ovarian cancer cells (Hudziak, et al., *Proc. Natl. Acad. Sci. USA* 85:5102 (1988); Lichtenstein, et al., *Cancer Res.*, 50:7364 (1990)), and those of natural killer cells (Wiltshle, et al., *Proc. Am. Assoc. Cancer. Res.*, 32:202 (1991)) or tamoxifen (Benz, et al., ibid.:211) in breast cancer cells. Therefore, $p185^{erbB-2}$ oncoprotein may have a central role both in the development and progression of human tumors, and constitutes a preferential therapeutic target in neoplasia when overexpressed and clinically associated with poor prognosis.

On the basis of its structural similarity with the extracellular domain (ECD) of the EGFR, the $p185^{erbB-2}$ ECD was thought to function in growth factor binding. Two candidate ligands for $p185^{erbB-2}$ have been so far purified: (i) a 30 kDa glycoprotein (gp30), secreted by MDA-MB-231 human breast cancer cells, that binds and phosphorylates both EGFR and $p185^{erbB-2}$ (Lupu, et al., *Science*, 249:1552 (1991) and U.S. application Ser. No. 07/528,438, filed May 25, 1990 abandoned), and (ii) a 75 kDa protein (p75), secreted from SK-Br-3 human breast cancer cells, that specifically binds and phosphorylates $p185^{erbB-2}$ (Lupo, et al., *Proc. Natl. Acad. Sci. USA*, 89:2287 (1992) and U.S. patent application Ser. No. 07/640,497, filed Jan. 14, 1991 abandoned). The further potency of these two proteins in acting on the proliferation of $p185^{erbB-2}$ overexpressing human breast cancer cells point out the role of gp30 and p75 as growth factors in mammary neoplasia. Since EGF and TFGα do not bind $p185^{erbB-2}$ (Schecter, et al., *Science*, 229:976 (1985); King, et al., *EMBO J.*, 7:164 (1988); and Stem, et al., EMBO J., 7:995 (1988)), $p185^{erbB-2}$ and EGFR ECDs appear to interact with both common and specific ligands. Thus, as with the EGFR and its ligands, the ligands for erbB-2 receptor are involved in the growth regulation of malignant cells.

According to the autocrine growth stimulatory pathway, malignant cells are capable of secreting a potent tumor growth factor in vivo. Thus, the growth factor ligand may be detected in body fluids, much like human chorionic gonadotropin or α-fetoprotein, and could be used as a tumor marker and a prognostic variable. Studies suggest that TGFα activity can be detected in body fluids of cancer patients and that its presence may provide important information concerning the biology of a patient's tumor (Stromberg, et al., *J. Cell. Biochem.*, 32:247–259 (1986); Twardzick, et al., *J. Natl. Cancer Inst.*, 69:793–798 (1982); Sherwin, et al., *Cancer Res.*, 43:403–407 (1983)).

SUMMARY OF THE INVENTION

The present invention relates to blocking peptides which bind or interact with the ligands of epidermal growth factor receptor or erbB-2 receptor. However, the blocking peptides specific for the erbB-2 receptor do not interact significantly with EGF or TGFα. Such interaction or binding by the blocking peptides of the invention prevent or inhibit the interaction between the receptor molecules and their corresponding ligands.

Because such ligands are involved in the proliferation of adenocarcinoma cells, the blocking peptides of the present invention may serve as a treatment for cancer. In particular, the blocking peptides of the invention can be used in a method for treating a number of cancers associated with erbB-2 transmembrane protein overexpression including, but not limited to, breast, ovarian, gastric, lung, prostate, salivary gland, and thyroid carcinomas.

The invention additionally pertains to the use of the blocking peptides of the invention to detect cells expressing $p185^{erbB-2}$ transmembrane protein or the EGFR transmembrane protein.

The invention is also directed to methods of obtaining the purified blocking peptides of the invention from cells which produce such peptides or by way of automated protein synthesis.

BRIEF DESCRIPTION OF THE DRAWINGS

Amino acid sequence information may be designated herein by the numerical position within the erbB-2 receptor or EGFR. The numbering of the amino acid sequence used herein is that described by Bargmann, et al., *Nature*, 319:226–230 (1986) and Yamamoto, et al.,*Nature*, 319:230–234 (1986), both of which are incorporated by reference in their entirety.

FIG. 2 shows $p185^{erbB-2}$ competition assays in SK-Br-3 cells in the presence of $p185^{erbB-2}$ homologous peptides. SK-Br-3 cells were placed in 48-well plates (Costar) in 5% fetal calf serum (FCS), IMEM (Biofluids). Cells were washed and incubated for 30 minutes at 37° C. with binding buffer [1 mg/ml BSA, 10 mM Hepes, 20 mM glutamine, DMEM-F12 pH 7.4]. Binding studies were performed for 3 hours at 4° C. On SK-Br-3 cells, 1 nM iodinated 4D5 was incubated with various concentrations of P1 (○), P2 (●), P3 (△), P4 (▲), RL1 (□), and RL2 (■) unlabeled peptides (A), or with unlabeled 4D5 (B). After incubation, cells were washed three times with binding buffer, and solubilized with 1% SDS. Unspecific binding of iodinated 4D5 was determined with an excess (100 nM) of unlabeled 4D5. Each group was assayed in triplicate. Experiments were performed three times with similar results.

FIG. 3 shows levels of autophosphorylation activity in MDA-MB-453 and MDA-MB468 cells treated with gp30 and RL1 or RL2 peptides. Cells were grown in 24-well plates (Costar) to 70% confluence in 5% FCS IMEM and serum-starved 24 hours prior to assays. Cells were then treated for 20 minutes at 37° C. with RL1 or RL2 with and without gp30 (at concentrations given below), as indicated on Figure panels, washed once with serum-free IMEM, and lysed at 4° C. for 10 minutes with a lysis buffer containing SDS (Emprotech). Total cellular proteins were subjected to 4–20% SDS-PAGE, and blotted onto Hybond-ECL membranes (Amersham). Membranes were blocked with trisbuffered saline [5% BSA, 0.5% Tween 20] and probed with 1 μg/ml phosphotyrosine monoclonal antibody (UBI) in tris-buffered saline [0.5% BSA, 0.5% Tween 20]. Immune complexes were detected using the ECL-western blotting kit (Amersham) as indicated by the manufacturer. Densitometric analyses were performed using a SAMBA 4000 system (Dynatech Laboratories). The values obtained were corrected for background and expressed as control percentages. Differences were considered significant when effects more than 10% versus controls occurred.

Upper panels correspond to MDA-MB-453 cells. Further probing of the same membranes with a $p185^{erbB-2}$ monoclonal antibody (Oncogene Science) showed identical levels of $p185^{erbB-2}$ expression over each blot. Lower panels correspond to MDA-MB-468 cells. Further probing of the same membranes with an EGFR monoclonal antibody (Oncogene Science) showed identical levels of EGFR expression over, each blot. gp30 was used at 50 pM. Lanes 1 to 4 correspond to increasing concentrations of RL2 (left panels), or RL1 (right panels) peptides. 1: 0.06 μM; 2: 0.6 μM; 3: 6 μM; 4: 60 μM. Experiments were repeated four times with similar results.

FIG. 4 shows phosphoaminoacid analysis of 185 kDa phosphoproteins in MDA-MB-453 cells treated with gp30 and RL2 ($p185^{erbB-2}$ homologous) peptide. MDA-MB-453 cells were grown in 35 mm dishes (Costar) to 70% confluence in 5% FCS IMEM. Cells were washed twice with $PO_4$ free DMEM (Gibco), and then incubated for 3 hours at 37° C. with [$^{32}P$]-orthophosphate (Amersham; 1.0 mCi/ml in each dish). Cells were then treated for 10 minutes at 37° C. with samples: control, 60 μM RL2, 50×10$^{-12}$M gp30, or 50×10$^{-12}$M gp30 plus 60 μM RL2. All samples were preincubated 30 minutes at 37° C. Cells were washed twice with PBS, and lysed at 4° C. for 10 minutes with a lysis buffer containing 1% Triton X-100, and kinase, protease and phosphatase inhibitors as described (Frackelton, et al., *J. Biol. Chem.*, 259:7909 (1984)). After centrifugation at 10,000× g for 15 minutes at 4° C., tyrosinephosphorylated proteins were isolated from supernatants by microbath affinity chromatography on the phosphotyrosine monoclonal antibody 1G2 (provided by Dr. A. R. Frakelton) as previously described (Frackelton, et al., *J. Biol Chem.*, 259:7909 (1984); and Beitz, et al.,*Proc. Natl. Acad. Sci. USA*, 88:2021 (1991)), eluted with 1 mM phenylphosphate in PBS pH 7.4, and purified further by immunoprecipitation with $p185^{erbB-2}$ monoclonal antibody Ab-3 (Oncogene Science) adsorbed on protein A-Sepharose. Tyrosine-phosphorylated p185$^{erbB-2}$ proteins were resuspended in 50 μl [50 mM Tris-HCl (pH 6.8), 2% SDS, 10% glycerol, 0.1% bromophenol blue, 5% β-mercaptoethanol] sample loading buffer, heated 5 minutes at 95° C., and resolved on a 7.5% SDS-PAGE. Bands corresponding to 185 kDa erbB-2 protein were excised out of the gel, subjected to partial acid hydrolysis and two dimensional thin-layer electrophoresis using HTLE-7000 (CBS Scientific Co.) as previously described (Cooper, et al., *Method. Enzymol.*, 99:387 (1983); Frackelton, et al., *Mol. Cell. Biol.*, 3:1343 (1983)). Densitometric analyses were performed as described above. Experiments were repeated four times with similar results.

FIG. 5 shows soft agar colony formation of MDA-MB-453 cells treated with p185$^{erbB-2}$ homologous peptides, and SK-Br-3 cells treated with RL2, gp30, and p75. MDA-MB-453 (A), or SK-Br-3 cells (B) were plated in 35 mm tissue culture dishes (Costar). A bottom layer of 1 ml IMEM containing 0.6% Bacto-agar (Difco), 2 mM glutamine, and 10% FCS was prepared. Top layers contained $2 \times 10^4$ cells and samples in 0.4% Bacto-agar, 10% FCS IMEM. Samples were sterilized prior to plating by filtration using 0.22 μM Millex CU millipore filter. The legend of peptide symbols in A is identical to the one in FIG. 2. The following concentrations were used in B: $5 \times 10^{-12}$M gp30, $2 \times 10^{-12}$M p75, 60 μM RL2, and 127 nM p185$^{erbB-2}$ extracellular domain (ECD) as positive control. Experiments were carried out in FCS that had been tested for optimal cloning efficiency. Cells were incubated 7–9 days in humidified 5% CO$_2$ atmosphere at 37° C. Colonies larger than 60-μm were counted using a Baush and Lomb Stem Cell Colony Counter (Artex Systems Corp.). Each group was assayed in triplicate. Experiments were performed three times.

FIG. 6A: EGFR binding competition assays were performed in MDA-MB-468 cells. In brief, 150,000 cells/well were plated in 24 well plate. The binding assays were performed as described by Lonardo, et al., *Mol. Cell. Biol*, 2:992 (1990). In brief, 1 nM iodinated EGF (Amersham) was incubated with increasing concentrations of RL2 or RL2-K (0.6, 6, 60 μM, respectively). Increasing concentrations of unlabelled EGF were used as control, as shown in the insert. Each group was assayed in triplicate. Values are from three experiments and expressed as the mean percent of control cases. The standard deviation on values did not exceed 10%.

FIG. 6B: EGFR Tyrosine Phosphorylation assays were performed using MDA-MB-468 cells, as described for FIG. 3. Cells, in the presence or absence of increasing concentrations of RL2-K or RL2, lanes 1–3 (0.6, 6 and 60 μM), respectively, were treated with EGF (1.68 nM) [RL2-K (upper panel) and RL2 (lower panel)]. The membranes were then striped and reprobed with an anti-EGFR monoclonal antibody (Oncogene Science) that indicated comparable levels of protein-expression over each blot.

DESCRIPTION OF THE PREFERRED EMBODIMENTS

In the description that follows, a number of terms used in the field of ligand-growth factor receptor interactions and recombinant DNA technology are extensively utilized. In order to provide a clear and consistent understanding of the specification and claims, including the scope to be given to such terms, the following definitions are provided:

Blocking Peptide. The term "blocking peptide" is meant to refer to a peptide or protein molecule which is capable of binding to or interacting in some way with a ligand of the erbB-2 transmembrane protein or a ligand of the epidermal growth factor receptor. However, blocking peptides with amino acid sequence found in the erbB-2 receptor may not significantly bind to epidermal growth factor (EGF) or transforming growth factor a (TGFα). Similarly, blocking peptides with sequence found in the EGFR may not bind to erbB-2 ligands. Binding or interaction of a blocking peptide of the invention with the corresponding growth factor or ligand results in the prevention or inhibition of the interaction between a ligand and its corresponding receptor. Because the ligand-receptor interaction is involved in the proliferation of erbB-2 and EGFR-expressing adenocarcinoma cells, the term "blocking peptide" is meant to include all peptides which adversely affect the interaction between the epidermal growth factor receptor or erbB-2 receptor and their corresponding ligands.

The term "blocking peptide" is not meant to include the wild-type EGFR protein or the p185$^{erbB-2}$ protein. Examples of blocking peptides include the extracellular domain (ECD) of EGFR or erbB-2 receptor or fragments thereof, such as subdomain III of ECD. Preferably, blocking peptides correspond to smaller fragments within subdomain III, such as the RL2 peptide described below. Alternatively, blocking peptides may be functional derivatives. Preferably, derivatives will contain the sequence of peptides RL2 or RL2-K but not the complete sequence of domain III. Most preferably, derivatives will be modified to resist proteolytic cleavage of the portion corresponding to RL2 or RL2-K. Typically, the blocking peptides of the invention range in size from 3 amino acids in length to 1000 amino acids in length. Preferably, the blocking peptides of the invention range in size from 3 amino acids to 100 amino-acids. More preferably, the blocking peptides of the invention range in size from 3 to 50 amino acids. Most preferably, the blocking peptides of the invention have at least 8 amino acids.

Mutant. As used herein, the term "mutant", is meant to include derivatives of a blocking peptide in which the amino acid sequence of the peptide has been modified in an manner resulting from addition, substitution, insertion or deletion of one or more amino acids. By a "biologically active mutant" of a blocking peptide is meant a mutant of the blocking peptide which retains all or some of the biological activity possessed by the blocking peptide, particularly the ligand binding activity. The term "mutation" may also be used as a general term to denote the modification of any DNA or RNA sequence by addition, substitution, insertion or deletion of one or more nucleotides within a particular sequence.

Functional Derivative. By a "functional derivative" of the blocking peptide of the invention is meant a peptide that possesses a biological activity which is substantially similar to the blocking peptide from which the derivative is derived. By "substantially similar" is meant a biological activity which is quantitatively similar but qualitatively different from the activity possessed by the original blocking peptide. By the phrase "a biological activity which is qualitatively similar" is meant a peptide which more or less retains the biological activity of the original blocking peptide. For example, a functional derivative of the original blocking peptide retains the ability to interact or bind with ligands of the p185$^{erbB-2}$ receptor or EGFR. The term "functional derivative" is intended to include biologically active "mutants," "fragments," and "variants," of the original blocking peptides of this invention. Examples of functional derivatives of the original peptide contemplated by this invention include, but are not limited to amino acid substitutions, amino acid cohesions and mutation and circularization of the peptide by addition of Cys residues at both ends of the molecule.

Fragment. A "fragment" of the blocking peptide is meant to refer to a peptide molecule which contains a portion of the complete amino acid sequence of the receptor protein whose activation is blocked by the blocking peptide. By a "biologically active fragment" of a blocking peptide is meant a fragment of the peptide which retains all or some of the biological activity possessed by the peptide. For example, if the fragment retains some or all of the ligand binding activity, then such fragment is said to be a biologically active fragment of the blocking peptide.

Variant. A "variant" of the blocking peptide of the invention is meant to refer to a peptide substantially similar in structure and biological activity to either the blocking peptide or to a fragment thereof, but not identical to such molecule or fragment thereof. A variant is not necessarily derived from the original peptide and may be obtained from any of a variety of receptors similar or different to EGFR or erbB-2 receptor.

Substantially Pure. The term "substantially pure" or "substantially purified" is meant to describe a protein or peptide which is substantially free of any compounds normally associated with a protein or peptide in its natural state, i.e., substantially free of contaminating protein and carbohydrate components. The term, however, is not meant to exclude artificial or synthetic mixtures of the protein or peptide. The term is also not meant to exclude the presence of minor impurities which do not interfere with the biological activity of the peptide or protein, and which may be present, for example, due to incomplete purification.

A. Ligands of the erbB-2 Transmembrane Protein and/or Epidermal Growth Factor Receptor Protein Lupu, et al.,. *Science*, 249:1552–1555 (1991) reported the identification and purification of an approximately 30 kilodalton (kDa) growth factor secreted by MDA-MB-231 human breast cancer cells. This glycoprotein (gp30) was purified to apparent homogeneity by sequential low affinity heparin-sepharose chromatography and by reversed phase chromatography. The gp30 ligand is also described in U.S. application Ser. No. 07/528,438, filed May 25, 1990abandoned. The gp30 glycoprotein binds to epidermal growth factor receptor (EGFR) and has some TGFα-related properties. In addition, purified gp30 stimulated phosphorylation of $p185^{erbB-2}$ in cells that overexpress $erb^{erbB-2}$, in contrast with TGFα and EGF which do not interact with $p185^{erbB-2}$. Surprisingly, gp30 inhibited cell growth in all cells that overexpressed erbB-2 (Lupu, et al., *Science*, 249:1552 (1990)). A monoclonal antibody (4D5) against the extracellular domain of $p185^{erbB-2}$ (Hudziak, et al., *Molec. Cell. Biol.*, 9:1165 (1989)) was able to compete with gp30 for binding to $p185^{erbB-2}$, indicating that the gp30 ligand recognized and bound to the 4D5 binding site.

A second erbB-2 ligand, p75 does not recognize or bind to EGFR, a highly homologous receptor to $p185^{erbB-2}$. The p75 ligand is disclosed in U.S. application Ser. No. 07/640, 497, filed Jan. 14, 1991 abandoned.

The p75 erbB-2 ligand is a 75 kilodalton protein (p75). Substantially purified p75 ligand competes with 4D5 (Hudziak, et al., *Mol. Cell. Biol.*, 9:1165 (1989)) and MO193 antibodies for $p185^{erbB-2}$ binding and induces phosphorylation of $p185^{erbB-2}$. In cell growth assays, cell proliferation and colony formation of cell lines overexpressing erb2 were inhibited with p75. Furthermore, p75 can reverse the antiproliferative effect of soluble erbB-2 extracellular domain.

Although at present no other ligands are known which bind to the erbB-2 transmembrane protein, it will be evident to those of ordinary skill in the art that other ligands may be found which interact with the blocking peptides of the invention. Thus, although the blocking peptides of the invention may prevent or inhibit the interaction of gp30 and p75 from binding to their receptors, the blocking peptides of the invention are not meant to be so limited and thus may prevent the interaction of ligands to epidermal growth factor receptor and erbB-2 receptor other than gp30 and p75. Identification of erbB-2 ligands may be accomplished according to U.S. application Ser. No. 07/640,497, filed Jan. 14, 1991, abandoned.

B. Preparation of Blocking Peptide

Blocking peptides, according to the present invention, are "capable of binding" a molecule if they are capable of specifically reacting with or have affinity for a molecule or ligand such that the blocking peptide will bind (covalently or non-covalently) to the ligand molecule in a manner which blocks (inhibits or quantitatively reduces) a biological activity of the ligand molecule. An example of a blocking peptide of the present invention is the extracellular domain of the erbB-2 transmembrane receptor or fragments thereof. Subdomain III and peptide fragments of this subdomain are of particular interest. Preferably, peptide fragments of the extracellular domain of $p185^{erbB-2}$ which bind to the erbB-2 ligand may be used, although the sequence of receptors related to the erbB-2 transmembrane receptor may also be used to prepare blocking peptides according to the invention. Such related receptors may include, for example, neu, c-kit, met or any transmembrane tyrosine kinases that have a structure reminiscent of growth factor receptors. Sequence comparisons for EGFR, erbB-2 receptor and neu receptor have been described (Bargmann, et al.,*Nature*, 319:226–230 (1986); and Yamamoto, et al.,*Nature*, 319:320–234 (1986)).

In the preferred embodiment, blocking peptides of the invention comprise the amino acid sequence of the $Leu^{453}$ to $Glu^{460}$ region of the erbB-2 receptor. However, as will be recognized, homologous regions from related receptors may comprise blocking peptides according to this invention. For example, the $Leu^{448}$ to $Glu^{455}$ region of EGFR, which corresponds to the $Leu^{453}$ to $Glu^{460}$ of erbB-2 receptor, can comprise a blocking peptide of the invention. The eight amino acid sequence of the $Leu^{453}$ to $Glu^{460}$ region of erbB-2 receptor (hereinafter called RL2 or RL2-R) is:

Leu-Gly-Leu-Arg-Ser-Leu-Arg-Glu(SEQ ID NO:1) while the eight amino acid sequence of the $Leu^{448}$ to $Glu^{455}$ region of epidermal growth factor receptor (hereinafter called RL2-K) is:

Leu-Gly-Leu-Arg-Ser-Leu-Lys-Glu(SEQ ID NO:2).

Amino acid substitutions can be made in the blocking peptide of the invention, so long as the blocking peptide still retains biological activity, e.g., specifically reacting with or having affinity for ligands to EGFR or erbB-2 receptor. Other mutations (substitutions, deletions and additions) to the above described sequences may be made by well known techniques and tested for biological activity, e.g., binding to a ligand as described herein.

The blocking peptides of the present invention may be prepared by a number of well known techniques. Synthetic peptides may be constructed using automated protein synthesizers. Alternatively, the blocking peptides of the invention may be generated through recombinant DNA techniques. For instance, a DNA molecule encoding the desired peptide sequence may be operably linked to a promoter and other regulatory sequences such that expression of said peptide can be obtained in a transformed host.

A desired blocking peptide may also be produced from cells which exhibit the receptor molecule. SK-Br-3 cells have been used to purify the extracellular domain of p185$^{erbB-2}$ (Alper, et al., *Cell Growth and Differentiation*, 1:591–599, 1990). Yamamoto,. et al., *Nature*, 319:230–234 (1986) describes cloning and expression of full length p185$^{erbB-2}$ gene. A plasmid containing the erbB-2 receptor gene can be obtained from the American Type Culture Collection, Rockville, Md. (Accession No. ATCC 57584). Plasmids encoding shorter sequences which retain the eight amino acid region disclosed above can be constructed from this plasmid using standard methods. Similar plasmids containing the EGFR gene are also readily available, and they may similarly be used in construction of plasmids encoding blocking peptides.

Using well known recombinant or automated techniques, a number of functional derivatives (including biologically active mutants, fragments and variants) can be prepared. Briefly, a DNA molecule which encodes the desired peptide can be mutated by conventional site directed mutagenesis of cloned DNA (Maniatis, et al., *Molecular Cloning, A Laboratory Manual*, second edition, Coldspring Harbor, N.Y. (1989)). Random chemical mutagenesis may also be used. In addition, peptides can be made with random or site-specific changes (additions, substitutions, and/or deletions) in the amino acid sequence using well known automated synthesizers.

Once derivatives of the blocking peptides are produced, it will be evident that the derivatives can be easily analyzed for binding activity to the ligands of receptors such as EGFR or erbB-2 receptor. As described in more detail in the Examples, binding competition assays, tyrosine phosphorylation inhibition assays, cell proliferation inhibition assays, or animal experiments using nude mice may be used to analyze additional peptides having the activity of or substantially similar activity to the blocking peptides of the invention.

It will also be understood by those of skill in the art that the blocking peptide of the present invention can be detectably labeled or conjugated with therapeutic agents by standard techniques well known in the art. Examples of detectable labels are described below which may be used to detectably label the blocking peptides of the present invention.

The term "therapeutic agent" as used herein is meant to refer to any molecule, chemical compound, protein, etc., which, when introduced in close association to a cell, is capable of killing, destroying, inhibiting the growth or reproduction of, or otherwise interfering in the normal physiology or metabolism of said cell in a manner not conducive to the cell's survival or reproduction. Examples of suitable therapeutic agents include cytotoxic drugs, toxins, isotopes, endocrine therapeutics and the like. Specific cytotoxic drugs that may be used include Adriamycyn, Cyclophosphamide, 5-Fluorouracil, Methotrexate, Cisplatin, Carboplatin, Vincristine, VP-16, Bleomycin, Mitomycin C, Nicotinamide, etc. Toxins may include Ricin A, Diphtheria, and Pseudomonas. Examples of elements from which suitable isotopes can be made include phosphate, indium, yttrium, and iodine. Examples of suitable endocrine therapies include diethylstilbestrol (DES), Tamoxifen, LHRH antagonizing drugs, progestins, anti-progestins, etc.

C. Assays for Detecting erbB-2 Ligand

The blocking peptides of the present invention may be used to detect the presence of the erbB-2 ligand. Thus, the blocking peptides of the invention may be employed in histology and biopsy to detect erbB-2 ligand expression in a patient suffering from breast, liver, ovarian, lung, colon carcinomas and the like. Such detection may be accomplished using any of a variety of assays. For example, by radioactively labeling the blocking peptides, it is possible to detect the erbB-2 ligand through the use of binding assays. Any number of assays can be developed, much like the well known immunoassay, except that a blocking peptide of the invention is used in place of an antibody. Fluorescent, enzyme, or other suitable labels may also be employed in such assays.

Alternatively, the detection of erbB-2 ligand may be accomplished by in vivo imaging techniques, in which the labeled blocking peptides are provided to a patient, and the presence of the breast, ovarian, liver, lung, or colon carcinoma which expresses erbB-2 ligand is detected without the prior removal of any tissue sample. Such in vivo detection procedures have the advantage of being less invasive than other detection methods and are, moreover, capable of detecting the presence of ligand-expressing cells in tissue which cannot be easily removed from the patient.

In accordance with the above-discussed assays, blocking peptides may be labeled using any of a variety of labels and methods of labeling. Examples of types of labels which can be used in the present invention include, but are not limited to, enzyme labels, radioisotopic labels, nonradioactive isotopic labels, fluorescent labels, toxin labels, and chemiluminescent labels. Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholine esterase, etc.

Examples of suitable radioisotopic labels will be readily apparent to one of skill in the art. Suitable non-radioactive isotopic labels for use in the present invention will also be known to one of ordinary skill in the art. Examples of suitable fluorescent labels include a fluorescein label, an isothiocyanate label, a rhodamine label, a phycoerythrin label, a phycocyanin label, an allophycocyanin label, an o-phthaldehyde label, a fluorescamine label, etc.

Examples of suitable toxin labels include diphtheria toxin, ricin, and cholera toxin. Examples of chemiluminescent labels include a luminal label, an isoluminal label, an aromatic acridinium ester label, an imidazole label, an acridiniu salt label, an oxalate ester label, a luciferin label, a luciferase label, an aequorin label, etc.

Those of ordinary skill in the art will know of other suitable labels which may be employed in accordance with the present invention. The binding of these labels to the blocking peptides of the invention can be accomplished using standard techniques commonly known to those of ordinary skill in the art. Typical techniques are described by Kennedy, et al., (*Clin. Chim. Acta*, 70:1–31 (1976)), and Schurs, et al., (*Clin-Chim, Acta*, 81:1–40 (1977)). Coupling techniques mentioned in the latter are the glutaraldehyde method, the periodate method, the dimaleimide method, and the m-maleimido-benzyl-N-hydroxy-succinimide ester method, all of which methods are incorporated by reference herein.

The detection of blocking peptides can be improved through the use of carriers. Well-known carriers include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to a ligand. Thus, the support configuration may be spherical, as in a bead, or cylindrical, as in the inside surface of a test tube, or the external surface of a rod. Alternatively, the surface may be flat such as a sheet, test strip, etc. Those skilled in the art will note many other suitable carriers for binding blocking peptides, or will be able to ascertain the same by use of routine experimentation.

The binding molecules (blocking peptides) of the present invention may also be adapted for utilization in an immunometric type assays, also known as a "two-site" or "sandwich" assay. In a typical immunometric assay, a quantity of unlabeled blocking peptide, is bound to a solid support that is insoluble in the fluid being tested (i.e., blood, lymph, liquefied, stools, tissue homogenate, etc.) and a quantity of detectably labeled soluble blocking peptide is added to permit detection and/or quantitation of the ternary complex formed between solid-phase blocking peptide, ligand, and labeled blocking peptide. It will be apparent to one of skill that antibodies may also be used in place of or combination with blocking peptides in the immunometric assays according to the invention.

Typical immunometric assays include "forward" assays in which the blocking peptide bound to the solid phase is first contacted with the sample being tested to extract the antigen from the sample by formation of a binary solid phase blocking peptide-ligand. After a suitable incubation period, the solid support is washed to remove the residue of the fluid sample, including unreacted ligand, if any, and then contacted with the solution containing an unknown quantity of labeled blocking peptide (which functions as a "reporter molecule"). After a second incubation period to permit the labeled molecule to complex with the ligand bound to the solid support through the unlabeled blocking peptide, the solid support is washed a second time to remove the unreacted labeled blocking peptide. This type of forward sandwich assay may be a simple "yes/no" assay to determine whether erbB-2 ligand is present or may be made quantitative by comparing the measure of labeled blocking peptide with that obtained for a standard sample containing known quantities of ligand. Such "two-site" or "sandwich" assays are described by Wide, at pages 199–206 of *Radioimmune Assay Method*, edited by Kirkbam and Hunter, E. & S. Livingstone, Edinburgh, 1970, except that the antibody would be replaced with a blocking peptide. Combinations of antibodies and blocking peptides may also be used.

In another type of "sandwich" assay, which may also be useful to detect the erbB-2 ligand, the so-called "simultaneous" and "reverse" assays are used. A simultaneous assay involves a single incubation step as the blocking peptide bound to the solid support and labeled blocking peptide are both added to the sample being tested at the same time. After the incubation is completed, the solid support is washed to remove the residue of fluid sample and uncomplexed labeled peptide. The presence of labeled blocking peptide associated with the solid support is then determined as it would be in a conventional "forward" sandwich assay.

In the "reverse" assay, stepwise addition of a solution of labeled blocking peptide to the fluid sample is followed by the addition of unlabeled blocking peptide bound to a solid support after a suitable incubation period is utilized. After a second incubation, the solid phase is washed in conventional fashion to free it of the residue of the sample being tested and the solution of unreacted block peptide. The determination of labeled blocking peptide associated with a solid support is then determined as in the "simultaneous" and "forward" assays.

As explained above, the immunometric assays for erbB-2 ligand require that the particular binding molecule be labeled with a "reporter molecule." These reporter molecules or labels, as identified above, are conventional and well-known to the art. No single enzyme is ideal for use as a label in every conceivable immunometric assay. Instead, one must determine which enzyme is suitable for a particular assay system. Criteria important for the choice of enzymes are turnover number of the pure enzyme (the number of substrate molecules converted to the product per enzyme site per unit of time), purity of the enzyme preparation, sensitivity of detection of its product, ease and speed of detection of the enzyme reaction, absence of interfering factors or of enzyme-like activity in the test fluid, stability of the enzyme and its conjugate, availability and cost of the enzyme and its conjugate, and the like. Included among the enzymes used as preferred labels in the immunometric assays of the present invention are peroxidase, alkaline phosphatase, beta-galactosidase, urease, glucose oxidase, glycoamylase, malate dehydrogenase, and glucose-6-phosphate dehydrogenase.

In addition, the materials for use in the assays of the invention are ideally suited for preparation of a kit. Such a kit may comprise a carrier means being compartmentalized to receive in close confinement one or more container means such as vials, test tubes, and the like. Each of said container means comprises one of the separate elements to be used in the method.

For example, one of said container means may comprise a bound blocking peptide. Such peptide may be bound to a separate solid-phase or directly to the inner walls of a container. A second container may comprise detectably labeled antibody or blocking peptide in lyophilized form or in solution.

The carrier may also contain, in addition, a plurality of containers each of which comprises different, predetermined and known amounts of ligand. These latter containers can then be used to prepare a standard curve from which can be interpolated the results obtained from the sample containing the unknown amount of ligand.

D. Uses of Blocking Peptides

The blocking peptides of the present invention have a multitude of therapeutic and diagnostic uses. For example, therapeutic uses may involve cancer therapy in a patient suspected of suffering from cancer or other related diseases. Specifically, blocking peptide of the present invention containing the eight amino acid sequence of RL2 may be used to treat patients that have adenocarcinoma cells which produce the erbB-2 ligand and/or overexpress the erbB-2 receptor proteins. Similarly, blocking peptide having the eight amino acid sequence of RL2-K may be used to treat patients that have adenocarcinoma cells which produce the EGF ligand and/or overexpress EGFR.

One type of treatment may involve the use of the blocking peptide coupled to a therapeutic agent. By administering an effective amount of blocking peptide having the eight amino acid sequence of RL2-R coupled with the therapeutic agent to a patient, the adenocarcinoma cells in the patient which express erbB-2 ligand can be growth inhibited or killed, thereby providing a treatment for cancer.

In accordance with the method of cancer treatment of the invention, the conjugated blocking peptide is capable of recognizing and binding to carcinoma cells due to the association of the carcinoma cells with the erbB-2 ligand. Without being limited, the mechanism of binding to the cancer cell may involve the recognition of erbB-2, ligand located on the cell surface or because of expression and/or secretion of the ligand.

Once the conjugated blocking peptide is bound or in close association with the adenocarcinoma cell by interacting with ligand, the therapeutic agent is capable of inhibiting or killing that cell. In this manner, the therapy of the present invention is selective for a particular target, e.g., cancer cells which are associated with the erbB-2 ligand.

Normal cells and other cells not associated with the erbB-2 ligand (cells which do not express or bind erbB-2 ligand) may not, for the most part, be affected by therapy with blocking peptide containing the eight amino acid sequence of RL2-R.

Alternatively, the blocking peptide of the present invention may be used to prevent or inhibit inducement of adenocarcinoma cell proliferation. For example, cancer cells which contain the $p185^{erbB-2}$ receptor are induced to proliferate in the presence of low concentrations of erbB-2 ligand. Preventing the erbB-2 ligand growth factor from interacting with its receptor may provide a means to treat a cancer patient.

According to the method of inhibiting or preventing cellular proliferation of the present invention, the blocking peptide is capable of binding to the erbB-2 ligand. Binding the excreted erbB-2 ligand in vivo forms a ligand-blocking peptide complex and thus may prevent or inhibit the ligand-receptor interaction either sterically or otherwise. Thus, the present invention provides a treatment to prevent or inhibit adenocarcinoma cell proliferation in a patient by administering an effective amount of a blocking peptide to such a patient.

It will be appreciated that a number of other therapeutic uses of the blocking peptides of the present invention may be devised. Such therapies may involve use of other known treatment techniques in combination with the blocking peptides of the invention. The present invention is not meant to be limited to the therapeutic treatment described and are thus only presented by way of illustration.

Furthermore, administration of an amount of the blocking peptides of the present invention sufficient to inhibit or kill an adenocarcinoma cell may vary depending upon a number of factors including the type of malignant cell, body weight of the patient, the type of therapeutic agent used and the like. Those of skill in the art will appreciate that the amount necessary to inhibit or kill a particular malignant cell in vitro or in vivo can easily be determined with minimal routine experimentation. An effective amount of such blocking peptides may be administered parenterally, subcutaneously, intravenously, intramuscularly, intraperitoneally or orally. In addition, pharmaceutical preparations may be prepared which contain suitable excipients, auxiliaries, or compounds which facilitate processing or stability of the blocking peptides of the invention as pharmaceutical agents.

Diagnostic uses of the blocking peptides of the present invention (due to its binding activity to ligands) may include, for example, detection of erbB-2 ligand in a sample obtained from a patient. Such samples may be body tissue, body fluids (such as blood, urine, tear drops, saliva, serum, and cerebrospinal fluid), feces, cellular extracts and the like.

According to the method of detecting erbB-2 ligands, the erbB-2 ligands are excreted in vitro into cell culture medium. Another growth factor, TGFα, also secreted in vitro was identified in body fluids of cancer patients. Consequently, the growth factor (erbB-2 ligand) may be detected in body fluids, stools, etc. from a cancer patient and thus be detectable using the assays of the invention.

Assaying for the erbB-2 ligand of the invention in a sample obtained from a patient may thus provide for a method for diagnosing cancer. That is, detection of erbB-2 ligand in a sample obtained from a patient indicates the presence of erbB-2 ligand expressing cells in a patient. Furthermore, since the blocking peptide is specific for, erbB-2 ligand, the assay may provide information concerning the biology of a patient's tumor. For example, cancer patients with adenocarcinoma cells that overexpress the erbB-2 receptor are known to have a much shorter disease-free period and poorer overall survival than cancer patients that do not show erbB-2 overexpression. Detection of erbB-2 ligand growth factor may thus serve as a prognostic test, allowing the clinician to select a more effective therapy for treating the patient. Similar assays may be used to detect EGFR ligands (EGF and TGFα) based on binding of EGFR blocking peptides.

Having now fully described the present invention, the same will be more clearly understood by reference to certain specific examples which are included herewith for purposes of illustration only, and not intended to be limiting of the invention, unless specified in the appended claims.

EXAMPLES

Example 1
Selecting a Small Peptide Which Binds Ligands

Figure 1:
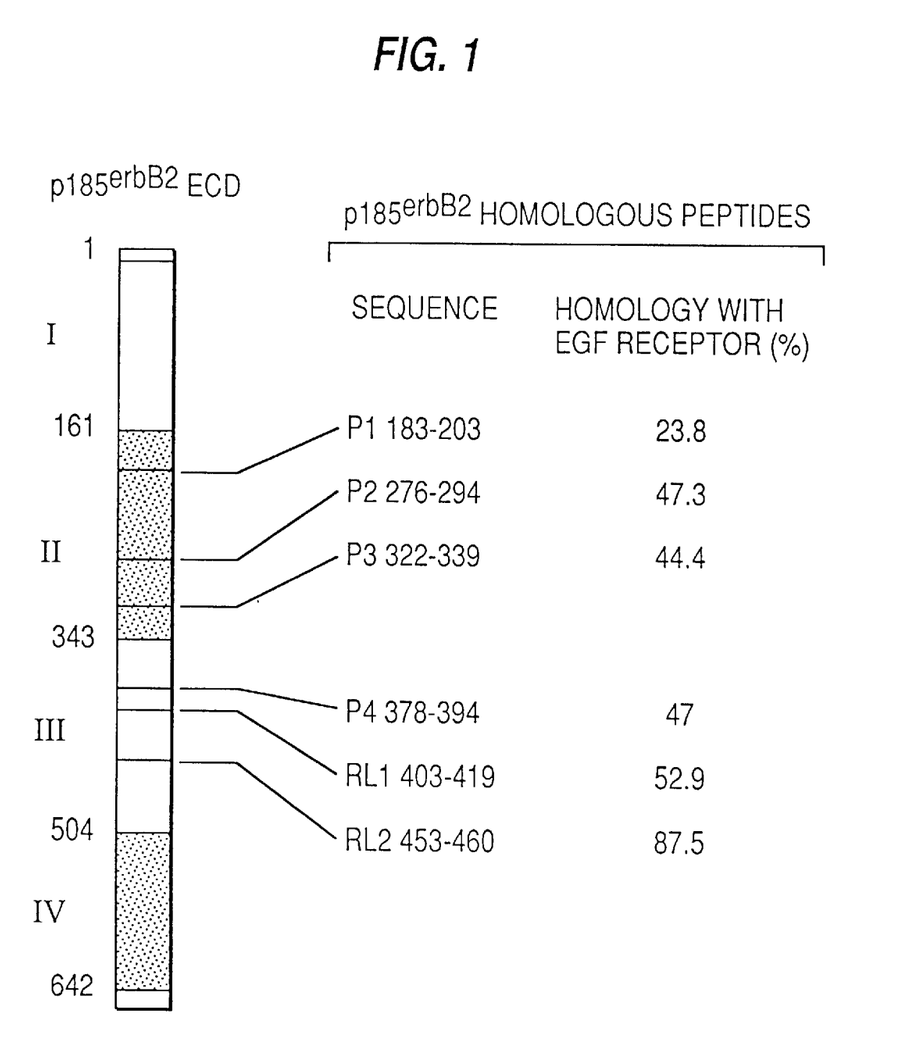
FIG. 1 shows the peptides of the $p185^{erbB-2}$ ECD used in bioassays on human breast cancer cell lines. Subdomains in $p185^{erbB-2}$ ECD are indicated by italicized numbers, indicating synthetic peptides P1, P2, P3, P4, RL1 and RL2. Percent homology of these peptides to the region of EGFR is also shown. Synthetic peptides RL1 and RL2 were obtained from the Peptide Synthesis Core Facility, Lombardi Cancer Center, Georgetown University Medical Center.

A four-domain model for the organization of EGFR-ECD has been proposed where the subdomain m contributes most of determinants involved in ligand interaction and signal transduction, the cysteine-rich flanking subdomains II and IV being in contact with each other and close to the plasma membrane (Ullrich, et al., *Cell*, 61:203 (1990); Lax, et al., *EMBO J.*, 8:421 (1989)). The $p185^{erbB-2}$ and EGFR-ECD sequences have diverged to result in an overall homology of 44% (Yamamoto, et al.,*Nature*, 319:230 (1986)). Surprisingly, we have discovered that the $p185^{erbB-2}$ extracellular subdomain m displays a short hydrophilic peptidic sequence, L453-E460, of 87.5% homology with its EGFR counterpart (one amino acid difference at K459). We felt this highly-conserved peptidic sequence may constitute a major determinant for the interaction of gp30 protein either with EGFR or $p185^{erbB-2}$ or EGFR-binding molecules such as monoclonal antibodies or growth factors. Together with the peptide corresponding to L453-E460 locus (RL2), two peptides corresponding to regions of decreasing homology in the subdomain III, and three peptides corresponding to sequences in the-subdomain II were also tested as controls (FIG. 1).

These peptides were evaluated for effects on the mitogenic signal transduction triggered by $p185^{erbB-2}$ or EGFR, in MDA-MB-453 or MDA-MB-468 human breast cancer cells respectively; alternatively, SK-Br-3 human breast cancer cells were also used. SK-Br-3 (ATCC HTB30), MDA-MB-453 (ATCC HTB131), and MDA-MB-468 (ATCC HTB132) cells were obtained from the American Type Culture Collection (ATCC, Rockville, Md.). As previously determined (Lupu, et al., *Science*, 249:1552 (1991), SK-Br-3 cells express high amounts of $p185^{erbB-2}$ and moderate levels of EGFR; MDA-MB-453 cells express high amounts of $p185^{erbB-2}$ and in detectable amounts of EGFR; conversely, MDA-MB-468 cells express high amounts of EGFR and indetectable amounts of $p185^{erbB-2}$.

To explore whether the RL2 peptide could specifically represent either a $p185^{erbB-2}$ or EGFR-extracellular binding site, we tested the aforementioned peptides in $p185^{erbB-2}$ or EGFR binding competition assays. Since iodinated gp30 was not available, $p185^{erbB-2}$ and EGFR competition assays were performed using iodinated monoclonal antibody 4D5 and iodinated EGF respectively. $p185^{erbB-2}$ monoclonal antibodies 4D5 and 7C2 were provided by Genentech, Inc., South San Francisco, Calif. 4D5 has been shown to induce tyrosine phosphorylation of p185$^{erbB-2}$ in SK-Br-3 human breast cancer cells, and growth inhibition of p185$^{erbB-2}$ overexpressing cells (Hudziak, et al., *Mol. Cell Biol.*, 9:1165 (1989); Kumar, et al., *Mol. Cell. Biol.*, 11:979 (1991)), whereas 7C2 (Fendly et al., *Cancer Res.*, 50:1550 (1990)) induces no biological response. The gp30 protein has been shown to compete with 4D5 for binding to p185$^{erbB-2}$, and with EGF for binding to EGFR, and to induce biological responses similar to those induced either by the 4D5 antibody in cells with p185$^{erbB-2}$ overexpression, or by EGF in cells with EGFR-overexpression (Lupu, et al., *Science*, 249:1552 (1991); Lupu, et al., Biochemistry, in press; Lupu, et al., *Proc. Natl. Acad. Sci. USA*, 89:2287–2291 (1992)).

Figure 2A:
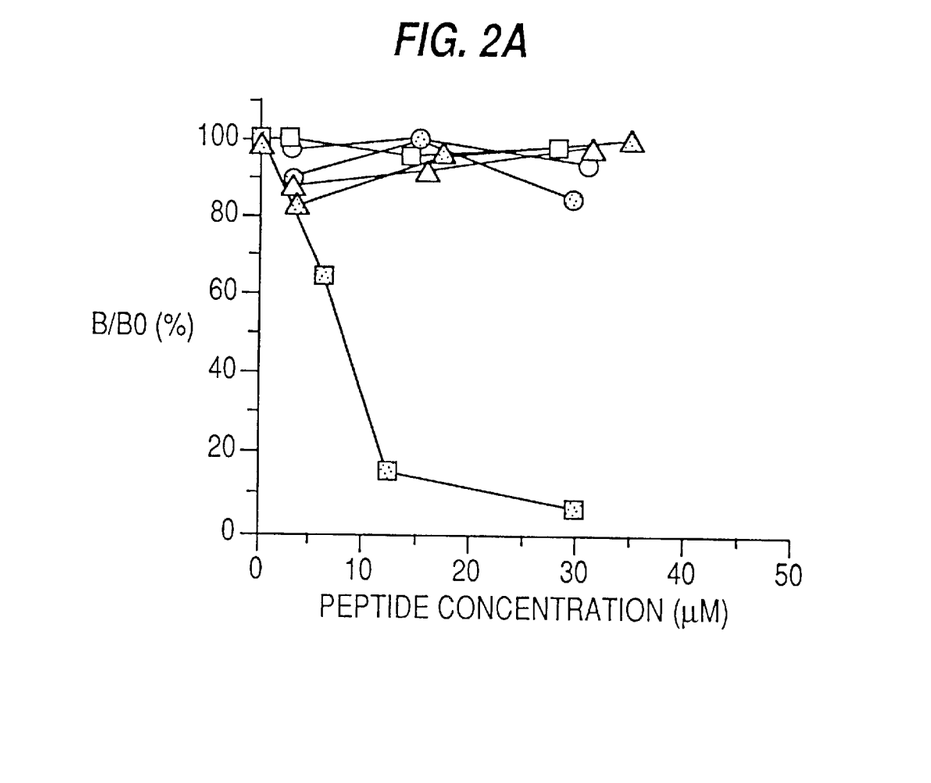
Figure 2B:
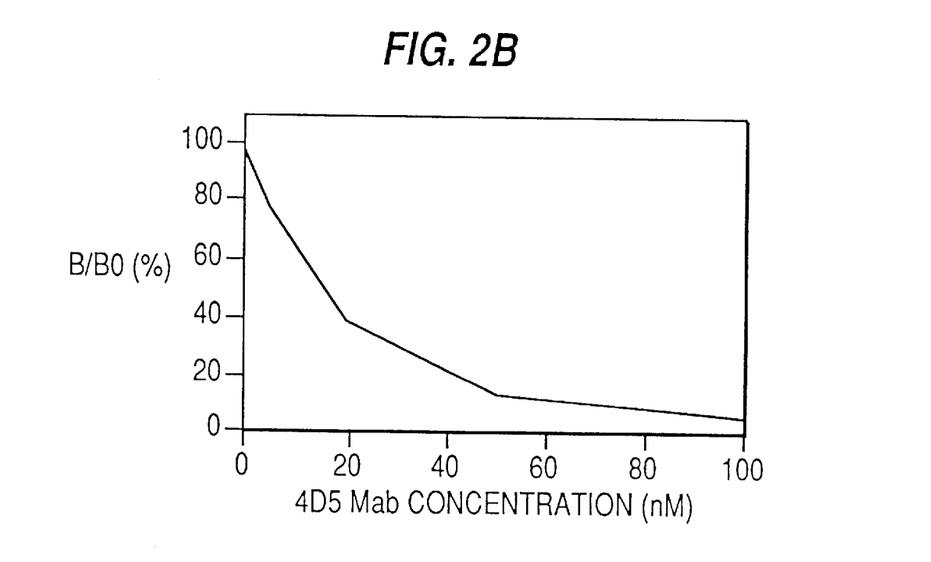

Among the peptides tested, only RL2 displaced in a dose-dependent manner (B/T 50: 8 μM) the binding of iodinated 4D5 to SK-Br-3 (FIG. 2). None of the peptides tested in the 2–40 μM range significantly affected either the binding of 1 nM control iodinated 7C2 antibody, or the binding of 1 nM iodinated EGF to MDA-MB-468 cells (not shown).

Iodinated RL2 was further shown to specifically bind to a 4D5-affinity column. First, RL2 peptide was iodinated using Iodogen, and purified with high-pressure liquid chromatography (HPLC); the specific activity was 26,000 cpm/μg peptide. Trichloroacetic acid (TCA) precipitation showed 98.8% yield. 3×10$^6$ cpm of iodinated RL2 were loaded onto a protein A-sepharose column coupled with 4D5 (coupling percentage: 98.5%). Elutions were performed with increasing concentrations of MgCl$_2$ from 1 to 5M (see Table 1). The specific elution marked as * on Table I was obtained at 2M MgCl$_2$. The flow-through contained only background levels of radioactivity.

TABLE 1

Binding of peptide to a 4D5 affinity column

| Samples | radioactivity (cpm) |
|---|---|
| Input | 3 × 10$^6$ |
| Flow through | 2.6 × 10$^5$ |
| Wash | 2.54 × 10$^5$ |
| 1M MgCl2 | 0.12 × 10$^5$ |
| | 9800 |
| | 5320 |
| 2M MgCl2 | 1.2 × 10$^5$ |
| | 1.2 × 10$^{6}$* |
| | 6.8 × 10$^5$ |
| 4M MgCl2 | 3.62 × 10$^5$ |
| | 0.38 × 10$^5$ |
| | 5800 |

*= Specific elution of iodinated RL2.

As a peptidic sequence recognized by 4D5, L453-E460 thus appeared as a possible major determinant for gp30 binding to p185$^{erbB-2}$. The absence of significant inhibition in EGF-binding to the EGFR suggesting no or lesser implications in gp30-binding to the EGFR.

Example 2
Effects of the Blocking Peptide on Phosphorylation

To further characterize RL2 blocking effects, we analyzed the homologous peptides for their ability to prevent the tyrosine phosphorylation induced by gp30 either in p185$^{erbB-2}$ or EGFR, or both of them. This study was first carried out using in vitro tyrosine phosphorylation assays for overall cases. In MDA-MB-453 cells, 0.06 to 60 μM RL2 strongly inhibited both baseline and gp30-stimulated levels of p185$^{erbB-2}$ tyrosine phosphorylation by 70 to 96% and 80%, respectively. (Densitometric analyses of autoradiograms were performed using a SAMBA 4000 system (Dynatech Laboratories). The values obtained were corrected for background and expressed as control percentages. Differences were considered significant when effects more than 10% versus controls occurred.)

Figure 3:
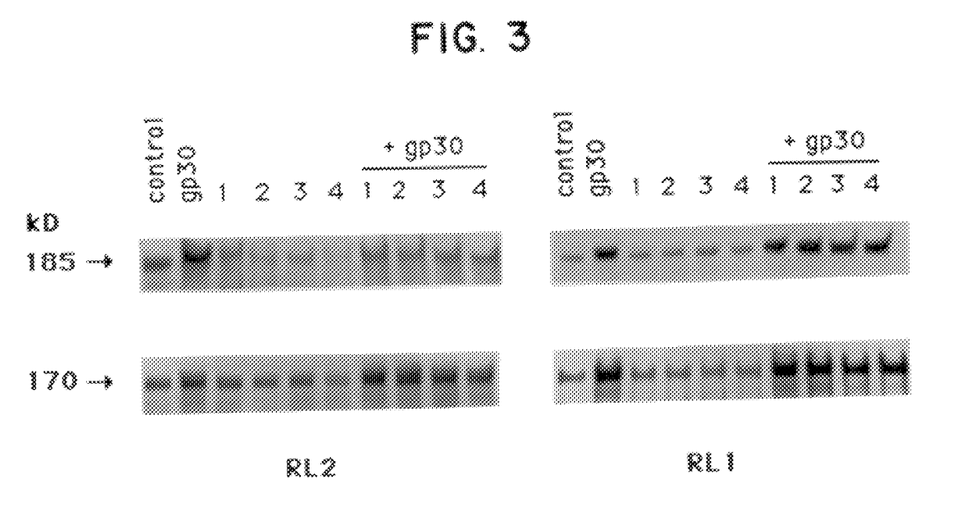
Figure 4:
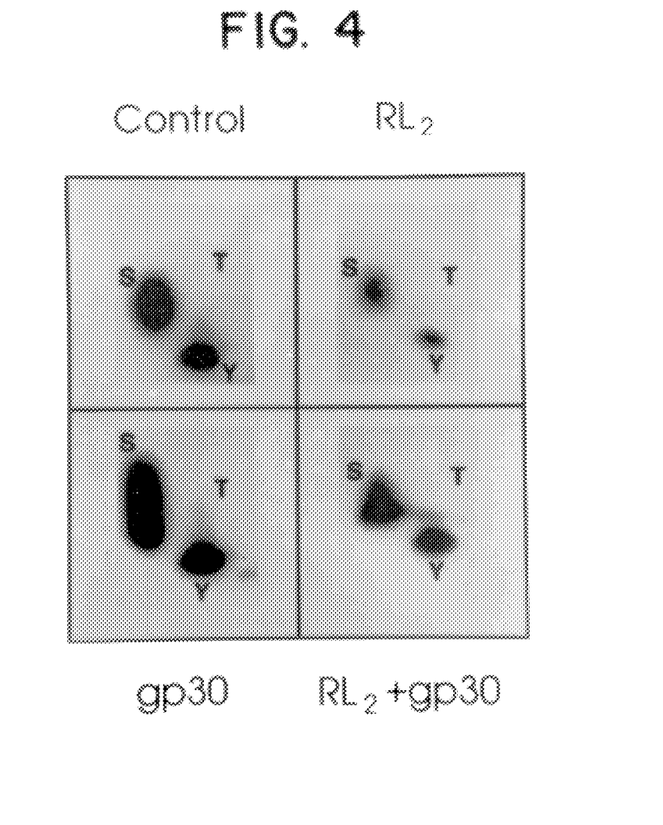

In MDA-MB-468 cells, 60 μM RL2 only inhibited the baseline level of EGFR tyrosine phosphorylation to a lesser extent (71%), but not the gp30-stimulated level. Similarly, RL2 showed no effect on EGF-induced tyrosine phosphorylation of EGFR in MDA-MB-468 cells. Although corresponding to a peptide sequence close to, and possibly cooperating with L453-E460, RL1 did not induce any significant inhibition when tested at similar concentrations (FIG. 3). The peptides P1, P2, P3 and P4 (30 μM) showed no effect (not shown). The specificity of RL2 blocking effects on p185$^{erbB-2}$ tyrosine phosphorylation was confirmed by in vivo phosphorylation assays and subsequent phosphoaminoacid analysis. The p185$^{erbB-2}$ tyrosine levels of phosphorylation were decreased both in absence and presence of gp30-stimulation by 50 and 26%, respectively (FIG. 4).

The foregoing demonstrates that RL2 interferes in the gp30 initiated activation of p185$^{erbB-2}$ exclusively, with no involvement in the gp30-initiated activation of the EGFR. Furthermore, the observation of RL2 inhibiting effects when used alone on MDA-MB-453 and MDA-MB468 cells suggests a basal level of presumed growth factors to be secreted, and act on p185$^{erbB-2}$ or EGFR phosphorylation through either full or partial interactions with the L453-E460 determinant.

Example 3
Effects of the Blocking Peptide on Proliferation

Figure 5A:
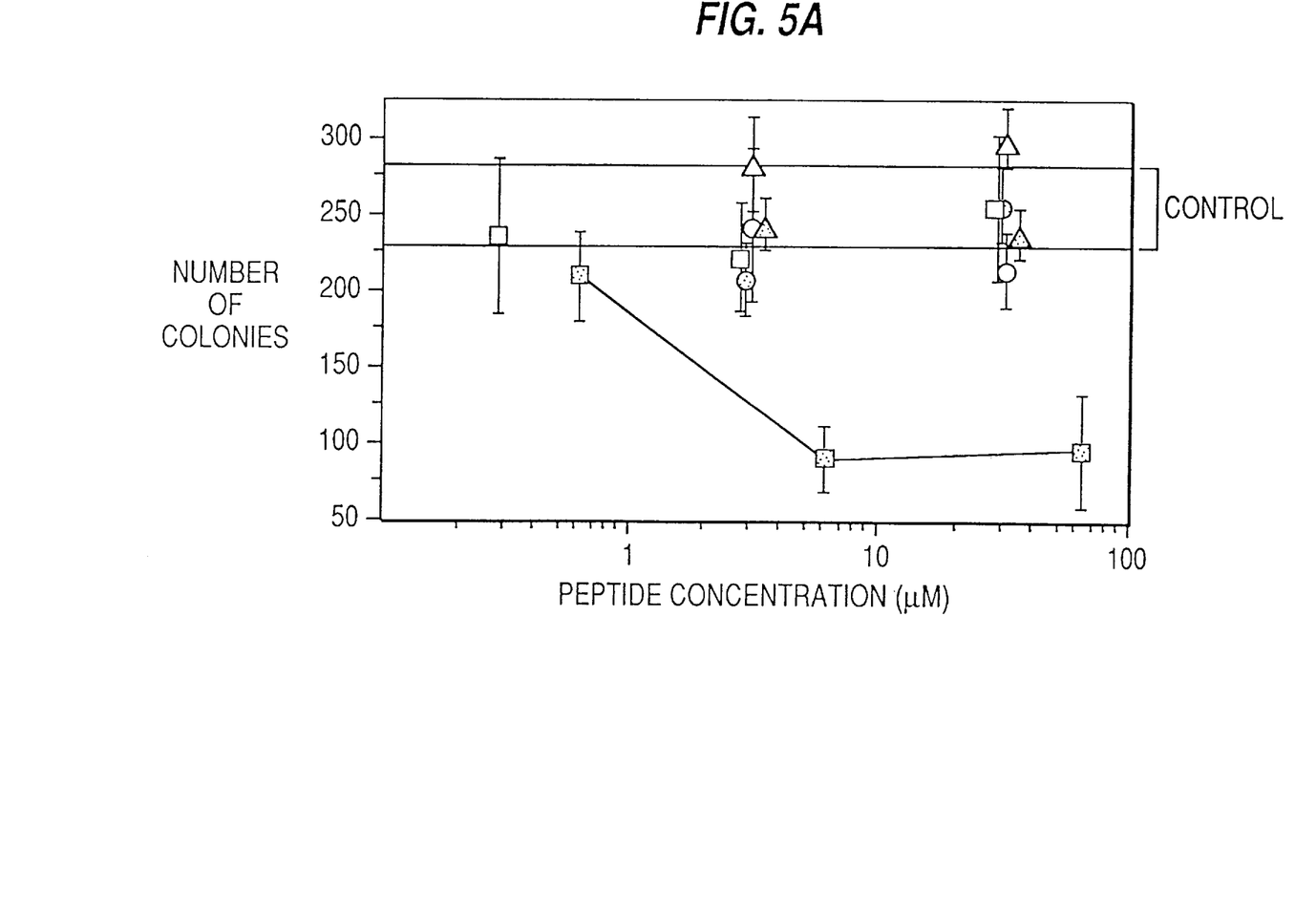

To test whether RL2 interferences at the level of p185$^{erbB-2}$ activation could result in inhibitions of p185$^{erbB-2}$ overexpressing cell proliferation, we evaluated the activities of p185$^{erbB-2}$ homologous peptides on the anchorage-independent growth of MDA-MB-453 cells. Given the RL2 effects previously observed on the basal level of EGFR tyrosine phosphorylation in MDA-MB-468 cells, this cell line was also tested regarding the possibility of further RL2 effects on EGFR-mitogenic signal transduction. The MDA-MB-453 cell anchorage-independent growth was inhibited by 72% in presence of 6–60 μM RL2 peptide, whereas P1, P2, P3, P4, and RL1 displayed no significant effect when tested at similar concentrations (FIG. 5A). MDA-MB-468 cells did not respond to any of the peptides, but did respond to 10 nM EGF which was used as positive control (not shown). Together with the lack of RL2 effect on both EGF binding displacement and gp30-stimulated EGFR tyrosine phosphorylation, this rules out the implication of the L453 to E460 determinant in EGFR mitogenic signal transduction.

Figure 5B:
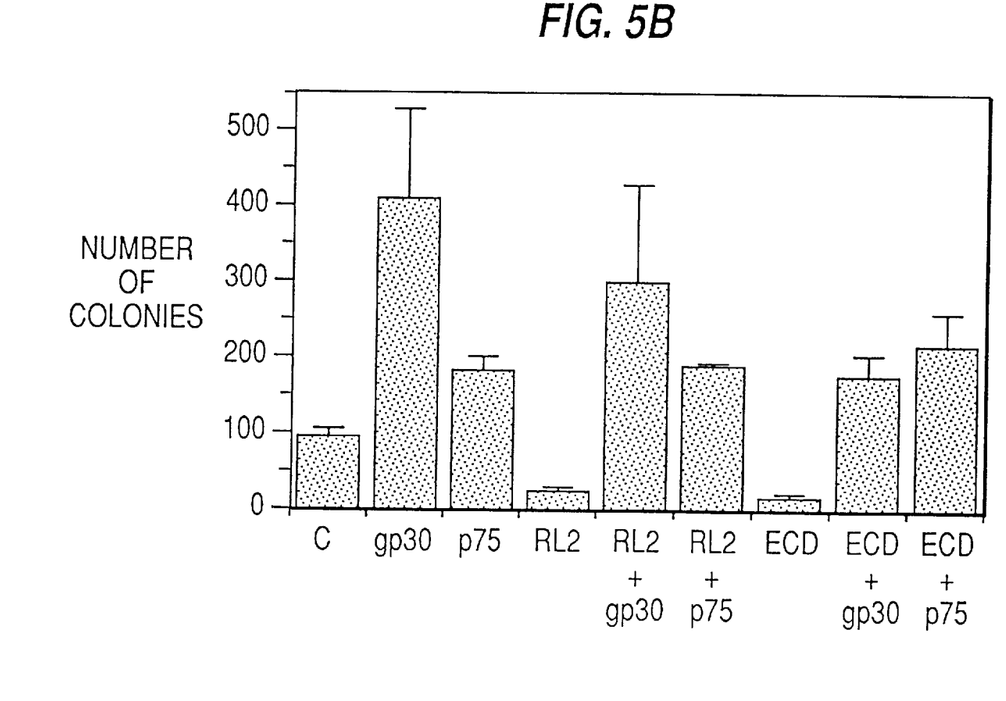

To illustrate RL2 antiproliferative effects as a blocking action on the p185$^{erbB-2}$ ligand-mediated effects, we tested this peptide and the ECD of p185$^{erbB-2}$ on the anchorage-independent growth of SK-Br-3 cells in the presence of stimulating concentrations of either gp30 or p75 proteins, the latter known to interact exclusively with p185$^{erbB-2}$ (Lupu, et al., *Proc. Natl. Acad. Sci. USA*, 89:2287–91 (1992)). The inhibiting effects of RL2 and p185$^{erbB-2}$ ECD were fully reversed by both gp30 and p75. The gp30 reversal on RL2 effectiveness confirmed the implication of the L453-E460 determinant in gp30 proliferating potency. Given that p75 is secreted by SK-Br-3 cells and competes with 4D5 monoclonal antibody for binding to p185$^{erbB-2}$ (Lupu, et al., *Proc. Natl. Acad. Sci. USA*, 89:2287–91 (1992)), the p75-reversal indicates that RL2 is an interfering agent in the autocrine regulation of p185$^{erbB-2}$-overexpressing cell proliferation (FIG. 5B).

Example 4
Blocking Peptide for EGF

RL2 and RL2-K differ only by one amino acid, in position 459-EGFR/454-erbB-2 (Lys/Arg). The absence of an effect of RL2 on EGF binding to EGFR in MDA-MB-468 cells showed that the 8-mer sequence derived from p185$^{erbB-2}$ has no effect on EGFR mitogenic signalling. The following experiment tested whether a synthetic peptide deriyed from the L448-E455 sequence of the EGFR (RL2-K) could specifically inhibit the EGFR signal transduction.

Figure 6A:
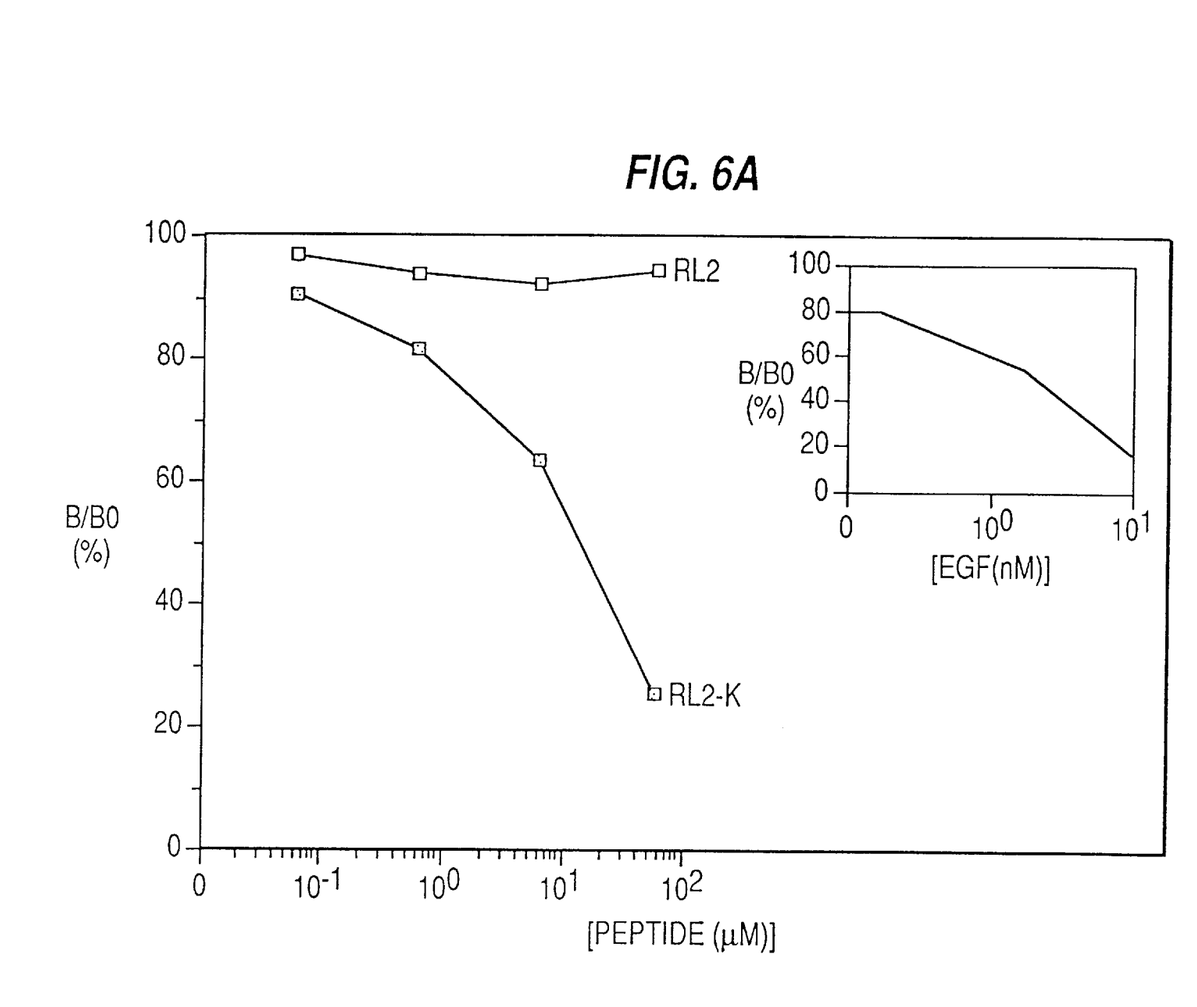
FIGS. 6A and B: Blockage of EGF signalling by RL2-K mediated through the EGFR in MDA-MB-468 cells.
Figure 6B:
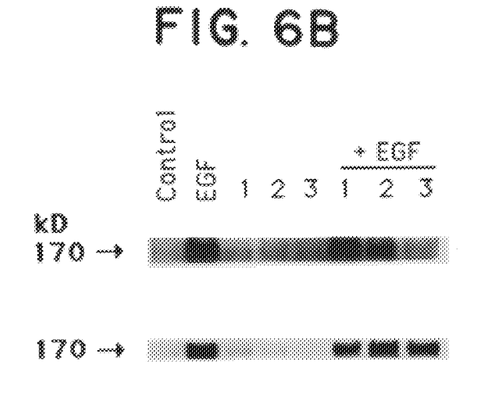

The effects of the peptides in MDA-MB-468 cells were studied for their effects on EGF binding, EGFR tyrosine phosphorylation, and colony formation (FIG. 6). Unlike RL2, RL2-K blocked the binding of iodinated EGF to the EGFR in a dose-dependent manner (FIG. 6A). In vitro assays showed that 6–60 μM RL2-K inhibited up to 85% the EGF stimulation of EGFR tyrosine phosphorylation, whereas RL2 had no effect (FIG. 6B). In contrast, RL2-K showed no significant effect when tested on colony formation of MDA-MB-453 cells (Table 2). Taken together, these results demonstrate that RL2-K specifically blocks EGFR signal transduction, and displays no effect on p185$^{erbB-2}$ activity.

TABLE 2

RL2 and RL2-K Effects On The Anchorage-Independent of MDA-MB 453 Cells

| Treatments* | Number of Colonies (± SD) |
|---|---|
| Untreated | 942 ± 120 |
| 33 nM 4D5 | 302 ± 96 |
| 6 μM RL2 | 245 ± 46 |
| 60 μM RL2 | 123 ± 21 |
| 6 μM RL2-K | 788 ± 109 |
| 60 μM RL2-K | 990 ± 92 |

*Cells were treated as indicated. The monoclonal antibody 4D5 (kindly provided by Genentech, CA) and the RL2 peptide were used as positive controls. Soft agar cloning assays were carried out as previously described (Lupu, et al., Proc. Natl. Acad. Sci. USA, 87:2287–91, 1992). Colonies larger than 69 μM were counted using a Baush & Lomb Stem Cell Colony Counter (Artex Systems Corp.). Each group was assayed in triplicate. Experiments were performed three times with similar results.

These studies suggest that the subdomain III of the extracellular domains of p185$^{erbB-2}$ and EGFR, respectively, is involved in growth factor binding, and that the specificity for growth factor binding to either receptor is attributable to a single amino acid difference at position 459/454. Arg in p185$^{erbB-2}$ and Lys in the EGFR are both positively charged amino acids commonly involved in protein-protein interactions. A variety of compounds mimicking the secondary structure of these determinants may display improved conformation stabilities and higher biological activities. p185$^{erbB-2}$ targeted therapies have been developed, such as monoclonal antibodies against its extracellular domain. The characterization of synthetic peptides corresponding to the binding site for growth factors in p185$^{erbB-2}$ and the EGFR provides an alternative strategy for treatment of human malignancies based on the design of new molecules to disrupt autocrine/paracrine loops defined by such overexpressed receptors and their ligands.

The biological significance of p185$^{erbB-2}$ overexpression that contributes to poor survival in breast, ovarian or gastric cancer has remained elusive. The constitutive kinase and transforming activity of p185$^{erbB-2}$ when overexpressed in NIH 3T3 cells (Lonardo, et al., Mol Cell. Biol., 2:992 (1990)) suggest the constitutive activation of p185$^{erbB-2}$ consequently to overexpression and the subsequent unbalanced growth stimulation of tumoral cells as a possible explanation. However, the secretion of p185$^{erbB-2}$ ligands with mitogenic properties by human breast cancer cell lines argues that p185$^{erbB-2}$ is fully implicated in the autocrine regulation of breast tumor growth. In this respect, the data disclosed herein indicate that the L453-E460 determinant is involved in the mediation of gp30 and p75 binding to p185$^{erbB-2}$. Thus, blocking peptides, such as the RL2 peptide, appear as new candidates to interrupt the autocrine loop involving the erbB-2 product.

Modification of the above-described modes for carrying out the invention that are obvious to persons of skill in medicine, immunology, hybridoma technology, pharmacology, and/or related fields are intended to be within the scope of the following claims.

All publications and patent applications mentioned in this specification are indicative of the level of skill of those skilled in the art to which this invention pertains. All publications and patent applications are herein incorporated by reference to the same extent as if each individual publication or patent application was specifically- and individually indicated to be incorporated by reference. Although the foregoing invention has been described in some detail by way of illustration and example for purposes of clarity of understanding, it will be obvious that certain changes and modifications may be practiced within the scope of the appended claims.

We claim:

1. A substantially pure cyclic peptide consisting of the amino acid sequence Leu-Gly-Leu-Arg-Ser-Leu-Arg-Glu circularized by addition of Cys residues at both ends of said peptide, said cylic peptide being capable of inhibiting phosphorylation of erbB-2 receptor.

2. A substantially pure blocking peptide consisting of the amino acid sequence Leu-Gly-Leu-Arg-Ser-Leu-Arg-Glu, said blocking peptide being capable of inhibiting phosphorylation of erbB-2 receptor.

* * * * *

UNITED STATES PATENT AND TRADEMARK OFFICE
CERTIFICATE OF CORRECTION

PATENT NO. : 5,874,528
DATED : February 23, 1999
INVENTOR(S) : Ruth Lupu et al.

It is certified that error appears in the above-identified patent and that said Letters Patent is hereby corrected as shown below:

Column 1,
Line 20, before "BACKGROUND OF THE INVENTION:" please insert the following:
-- This invention was made using U.S. government grant award No. P50 CA58185. Therefore the U.S. government retains certain rights to the invention. --

Signed and Sealed this

Twenty-eighth Day of December, 2004

JON W. DUDAS
*Director of the United States Patent and Trademark Office*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
  ( A ) LENGTH: 8 amino acids
  ( B ) TYPE: amino acid
  ( D ) TOPOLOGY: linear  ( i i ) MOLECULE TYPE: peptide  ( v ) FRAGMENT TYPE: internal ( v i ) ORIGINAL SOURCE:
                ( A ) ORGANISM: Homo sapiens ( x i ) SEQUENCE DESCRIPTION: SEQ ID NO:1:

Leu  Gly  Leu  Arg  Ser  Leu  Arg  Glu
        1                   5

( 2 ) INFORMATION FOR SEQ ID NO:2:

( i ) SEQUENCE CHARACTERISTICS:
                ( A ) LENGTH: 8 amino acids
                ( B ) TYPE: amino acid
                ( D ) TOPOLOGY: linear ( i i ) MOLECULE TYPE: peptide ( v ) FRAGMENT TYPE: internal ( v i ) ORIGINAL SOURCE:
                ( A ) ORGANISM: Homo sapiens ( x i ) SEQUENCE DESCRIPTION: SEQ ID NO:2:

Leu  Gly  Leu  Arg  Ser  Leu  Lys  Glu
        1                   5